United States Patent [19]

Frey et al.

[11] 4,309,757
[45] Jan. 5, 1982

[54] METHOD FOR CLASSIFICATION OF SIGNALS BY COMPARISON WITH AN AUTOMATICALLY DETERMINED THRESHOLD

[75] Inventors: Raymond Frey; Rudolf Voellmy, both of Zürich, Switzerland

[73] Assignee: Contraves Limited, Zürich, Switzerland

[21] Appl. No.: 99,646

[22] Filed: Dec. 3, 1979

[30] Foreign Application Priority Data

Dec. 19, 1978 [CH] Switzerland .............. 12907/78

[51] Int. Cl.³ .............................. G06F 15/42
[52] U.S. Cl. .............................. 364/416; 364/555; 364/300
[58] Field of Search ............ 364/416, 555, 408, 300

[56] References Cited

U.S. PATENT DOCUMENTS

| | | | |
|---|---|---|---|
| 3,557,352 | 1/1971 | Hogg et al. | 364/555 |
| 3,944,797 | 3/1976 | Coulter | 364/555 |
| 4,063,309 | 12/1977 | Hennessy et al. | 364/555 |
| 4,128,884 | 12/1978 | Engleand | 364/555 X |

*Primary Examiner*—Edward J. Wise
*Attorney, Agent, or Firm*—Werner W. Kleeman

[57] ABSTRACT

A method of separating signal classes in a stored signal quantum or set of signals correlated to a histogram in that there is looked for the minimum between two neighboring signal classes by mutual comparison of the stored signal values in a partial range of the histogram and there is stored as a separation threshold the characteristic of the thus determined channel characterizing the minimum, so that there can be differently evaluated signal values at different sides of such separation threshold. The invention is preferably used for particle analysis in haematology.

10 Claims, 2 Drawing Figures

METHOD FOR CLASSIFICATION OF SIGNALS BY COMPARISON WITH AN AUTOMATICALLY DETERMINED THRESHOLD

BACKGROUND OF THE INVENTION

The present invention broadly is in the field of medical applications, and, more specifically, relates to particle analysis with electronic, optical or mechanical means and, in particular, is concerned with the field of analysis of blood particles.

It is extremely problematic to analyse a mixture of particles of different size depending upon the distribution of the prevailing classes. What is meant herein by the expression distribution as used in this disclosure, is a discrete distribution of body volume and, in the narrower sense of a histogram, the frequency of the body volumes. In the statistical sense the histogram or the distribution is the probability density that a feature or characteristic, as to its value, will lie within a predetermined interval. The characteristics or features can be of different nature, for instance physical, chemical, morphological and others. If interest is only expressed in the particle count of a certain class, which ideally is present isolated from the distribution of other classes, then the analysis is unambiguous. Prevailing errors usually are attributable to the employed equipment and the accuracy is only limited by the signal-to-noise ratio inherent for the employed system. However, as soon as there are present mixed distributions, wherein, for instance, the same size particles of different particle species or classes belong to a respective inherent distribution density, then there are required criteria for discriminating between the overlapping distributions.

If for such a mixed distribution it is known that all classes are normally distributed, then, for instance, the finite number of classes can be determined according to a method disclosed by G. Doetsch. Yet, practice of this method is extremely cumbersome and presupposes that the mixed distribution is already known through knowledge of the mean value and the variance. However, with the here interesting fields of application there is usually only known an empirical distribution. In this case, for instance, the probability paper furnishes a raw method or technique in order to determine the one mixed distribution of exactly two classes by appropriately trying the possibly basically prevailing normal distribution.

With the heretofore known particle analysis equipment there are employed the human efforts of the operator in order to separate certain ranges of a mixed distribution of the body volume. The operator evaluates the distribution spectrum or a function derived therefrom, which spectrum has been obtained in a not here further described manner, and based upon criteria which the operator selects determines a "separation threshold", below which, for instance, the particles are allocated in accordance with their size to one class and above which the particles are then allocated to the other class. The once selected threshold is impressed upon the system, the particle analyser then only detects, for instance, the signals related to the particles which are below or above this threshold. Assuming the signals below the threshold are predicated upon spurious particles, the signals above the threshold upon particles which must be analysed, then the set threshold constitutes a discriminator for spurious and useful signals. If there are measured distributions of a number of size classes, then there must be selected a correspondingly greater number of separation thresholds which must be impressed upon the measuring system, provided that the individual classes are satisfactorily separated in order to be even able to detect a mixed distribution. This also is true for a bimodal mixed distribution.

Now if a particle analyser is employed for a special purpose, in other words for a limited field of application, say, for blood particle analysis, then in a great many types of equipment the thresholds are fixed in order to separate the particles which should be counted or measured from the particles which should not be incorporated into the measurement.

The setting of separation thresholds in a multimodal distribution curve, in the first instance leads to truncated distributions. The degree of truncation has a direct influence upon the integral over the distribution density, for instance upon the result of a count, and determines, usually dominantly, its accuracy. This is only valid if one stays with the truncated distribution without adequately correcting the same. If the distribution curve changes at the region of a fixed threshold, then by virtue of the increasing or decreasing truncation of the distribution to be analysed there is also altered the result of the analysis. While with prior faulty placement of the separation threshold it is possible for the result to become more accurate, normally however the opposite is true; the obtained result becomes poorer because the threshold previously usually was optimumly set. If, for instance, a particle analyser is designed for volume distribution analysis and for counting erythrocytes in human blood, that is to say, all of the sampled signals emanating from particles of a predetermined particle size interval should contribute to the measurement and a separation threshold should eliminate from the measurement those signals predicated upon artifacts, in other words, particles which are not erythrocytes, then this analyser, apart from possible exceptions, cannot be used, without correction of the threshold, for the counting of erythrocytes in animal blood. If the signal-to-noise ratio of the particle analyser is insufficient, then the physiologically possible variation range of the cell sizes in human blood already requires an individual accommodation of the threshold to each individual blood sample. Such analyser cannot be used at all for the analysis of just any random particles.

There will be clearly recognized from the foregoing the extremely narrow range of application with respect to a distribution function and, additionally, with insufficient signal-to-noise ratio the critical behaviour of a particle analyser with fixedly set separation thresholds.

System designs have been proposed wherein particle analysers are structured in such a manner that the operator, as required, can set the separation threshold or thresholds with the aid of a device mounted externally of the equipment. What previously was the task of an operator who was specially trained, now must be accomplished in equally exact and good quality by the particular random user of the equipment. The so-called setting or adjustment instructions should enable positive "setting" of a desired separation threshold by the user, without such manipulations falsifying the analysis results. Such setting instructions frequently are very simple, but, on the other hand, performance thereof is difficult and unreliable.

Thus, the threshold positioning or setting with the aid of an oscilloscope, where there are visible the particle signals and can be separated by varying a discriminator or threshold, delivers poorly reproducible values. Another recommended procedure requires the determination of a summation distribution curve. This is obtained by plotting counting results as a function of the threshold position. In the ideal case there is formed a horizontal segment, the so-called plateau, on the basis of which there can be set the threshold. The less the segment or plateau deviates from the horizontal and the greater its range, that much greater is the signal-to-noise ratio of the analyser. In the practical field of blood particle analysis the plateau, however, does not have any horizontal section and is also narrowly limited in range.

Positioning of the threshold on the basis of the determined curve is unreliable. In addition thereto, there must be considered the quite appreciable expenditure in time for the determination of the summation distribution curve, considering the fact that it must be periodically plotted and separately for erythrocytes and leukocytes. Additionally, the cell suspensions which are to be analysed are frequently unstable, something not known to many users. Consequently, the summation distribution curve is falsified and the threshold positioning based thereon is questionable. A possible solution from this dilemma is to improve the signal-to-noise ratio of the analysis system; through the use of sensors and a greater amount of electronic hardware it is possible to obtain a sub-critical threshold positioning. A further possibility is an adaptive threshold accommodation or setting.

Such threshold accommodation or setting is known from French Pat. No. 2,097,763. This patent discloses how to determine the transition between two overlapping distributions of signals. There are described means, with the aid of which there can be determined whether and in which channel of a histogram the stored frequency is smaller than the frequency stored in both directly neighboring channels. This known system serves for the determination of a local brightness extreme in a brightness field by finding and recognizing a characteristic object in a viewing field, wherein it is mentioned that the object can be a blood particle. The procedure which is followed is such that, after storing a complete histogram the counters of the individual channels are synchronously indexed or incremented until they are filled and in this state remain blocked. There is then determined which counter was the last to be filled. That is the counter of the channel where there is located the sought-for extreme. As will be apparent, with this procedure the histogram is extinguished, and therefore there is no longer possible an analysis of the signal distribution. In fact with this known teaching the procedures are carried out in two steps: in a first step there is determined, during the recording of a first histogram, the extreme and a threshold is set, then during a second step the histogram is again recorded and with the aid of the now set threshold evaluated. This procedure, where the first predetermined histogram is extinguished, is only capable of being used with those types of measurements where there is sampled an image which does not appreciably change as a function of time, whether such be the brightness image of a target position finder or homing device for navigation purposes, whether such be the image of a blood particle in the field of a microscope. The described procedure is not usable if there is not available an image which does not change as a function of time, for instance, if the signals are not brightness signals, rather designate the size of a particle in a particle suspension. In a particle analyser for use in a medical laboratory the histogram is formed rather slowly. With series tests it is important to maintain as short as possible the duration of each individual analysis, and therefore it is undersirable to perform each analysis twice (once in order to set a threshold, the second time in order to evaluate the histogram). Additionally, when proceeding according to the teachings of the aforementioned French Pat. No. 2,097,763 there is required twice the quantity of the particle suspension which is to be analysed than with a conventional particle analysis. This is prone to incur criticism by the potential customer of the analysis system.

SUMMARY OF THE INVENTION

Therefore, with the foregoing in mind it is a primary object of the present invention to provide a new and improved method for classification of signals which is not afflicted with the aforementioned drawbacks and shortcomings of the prior art proposals.

Another and more specific object of the present invention aims at a method wherein, during the analysis of particles with a brimodal mixed distribution of the particle sizes, there can be realized automatic finding of the threshold value in order to differentiate between overlapping size distributions, without there being necessary a longer time or a larger quantity of particle suspensions in comparison to conventional monomodal particle analysis.

Now in order to implement these and still further objects of the invention, which will become more readily apparent as the description proceeds, the method for the determination of a separation threshold for separating at least two signal classes in a signal quantum, composed of individual signals, converted by a feeler or sensor element into electrical signals and stored in a storage medium or memory, is manifested by the features that the stored signal quantity available for analysis is correlated into a histrogram in a memory organized into K-channels. Within a coherent number of N-channels of the histogram there is determined, by mutual comparison of the signal values stored in the N-channels or values derived therefrom, one of these channels whose signal value is the smallest. Thereafter, the characteristic value correlated to the thus determined channel is stored as separation threshold within the histogram, so that signal values to different sides of such separation threshold can be differently evaluated. The signal value of the determined channel is compared with each of the signal values of a multiplicity of $P_L$-channels directly following the one side of the determined channel and with each of the signal values of a multiplicity of $P_R$-channels directly following the other side of the determined channel. If in the immediately preceding step at least one of the signal values in the $P_L$ or the $P_R$ channels is smaller than the signal value of the determined channel, there is then repeated the aforementioned method step where there is determined the smallest signal value of the N-channels, with a different selection of N-channels, until the signal value of the determined channel is smallest.

Advantageously, with the inventive method it is particularly possible to use a thus operated analysis device in a wide band mode as concerns its distribution spectrum, since it automatically accommodates itself over a wide variation range to the size distribution. Additionally, the measuring integrity and thus, the analysis accuracy also is maintained even if the equipment is operated by less skilled personnel, and this advantage is not realized at the expense of longer analysis procedures or large quantities of the sample to be analysed.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
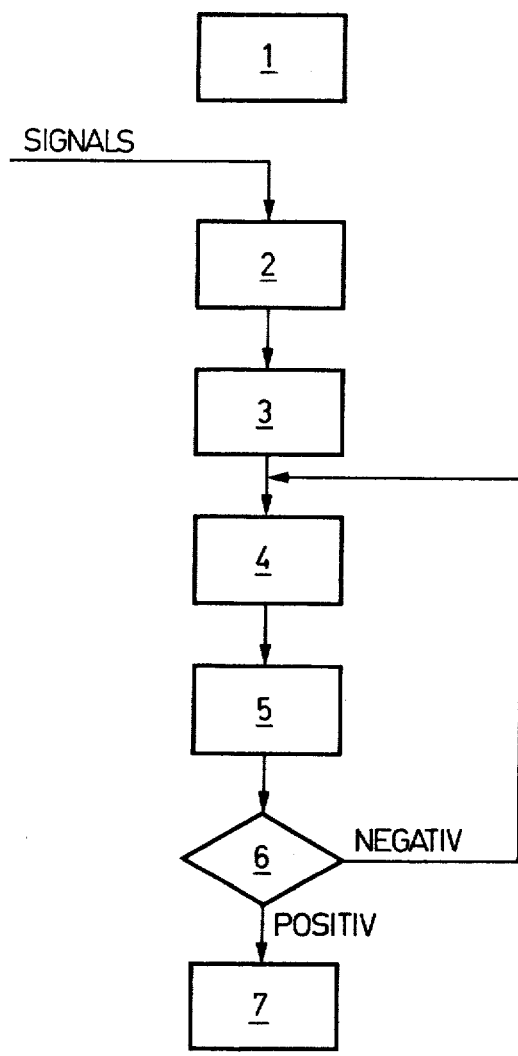
FIG. 1 shows as a flow diagram advantageous procedures when employing digital means.

Describing now the invention in detail, it is here mentioned that the description thereof will be carried out on the exemplary basis of blood particle analysis. There should be determined the size distribution of a number of erythrocytes in human or animal blood. It is well known that erythrocytes in human blood form a typical size class of 40 to 130 fl (fl=femtoliter), and the maximum of the distribution is approximately at 80 fl. On the other hand, the erythrocytes in the blood of a domestic cat form a typical size class of 20 to 80 fl and the maximum is at approximately 45 fl. The following table shows the typical erythrocyte distributions in blood of a number of different species.

| | Class (fl) approx. 95% of all particles | Lower Limit | Maximum |
|---|---|---|---|
| Human | 40–130 | 35 | 80 |
| Cat | 20–80 | 15 | 45 |
| Dog (female) | 30–120 | 25 | 60 |
| Guinea Pig | 40–130 | 30 | 70 |
| Mouse | 25–80 | 20 | 45 |
| Horse | 25–80 | 20 | 40 |
| Foal | 15–70 | 10 | 35 |
| Cow | 25–80 | 20 | 45 |
| Calf | 15–70 | 10 | 35 |

Almost each of these erythrocyte analyses requires, upon changing the species, the previously mentioned time-consuming conversion of the separation thresholds. Within the human range there is normally not expected large deviations of the erythrocyte distribution, however if there is considered such tasks in the veterinary field then it will be apparent that the automatic location and setting of the separation thresholds not only facilitates the work, but also extensively maintains constant the analysis reliability, especially when performing routine series analysis.

There is advantageously utilized for analysis purposes a prepared sample of a liquid containing erythrocytes which is then fed through a sampling zone, wherein the sampling means can be electrical or optical. The particles suspended in the liquid are sampled during their passage through the sampling zone, and the pulses or signals, produced in accordance with the sampled particles, possess different characteristics as a function of the physical properties of the sampled particle type.

During the analysis of leukocytes an advantageous preparation technique resides, among other things, in removing the erythrocytes which are present in higher concentrations, typically by about 1,000-fold, by means of haemolysis. With this treatment the erythrocytes are specifically destroyed and in the solution to be examined there is present a multiple 1,000-fold higher concentration of cell fragments of the destroyed erythrocytes in relation to the morphologically altered but intact leukocytes. These fragments form, or at least they should form, a different size class than the leukocytes. Roughly considered there is present a bimodal mixed distribution. In the ideal case the distribution of the artifacts, here the fragment particles, is clearly separated from the distribution of the leukocytes and separation of both distributions by a separation threshold leads to a truncated distribution of the leukocytes with a very small degree of truncation; any subsequent correction is superfluous.

Practical applications have shown that results from an uncorrected, truncated distribution are usable even in the presence of pronounced overlapping mixed distributions, but in any event at lest the truncation degree or a value derived therefrom should be given as the "quality criterion" of the analysis result. It is exactly in erythrocyte analysis where the deviation from an approximate normal distribution constitutes evidence of certain pathological changes and can be used in graphical portrayal as a further result of the analysis. The consequence of this is that: classes with pronounced deviation from the normal distribution cannot be positively corrected, even with usually complicated computation methods incorporated into the analysis. The result of a truncated distribution together with a quality criterion is more readily susceptible to evaluation than an inadequately corrected result. Thus, in practice, there is usually dispensed with correction of the truncated distribution.

Predetermination of a separation threshold without knowledge of the distribution of the incoming signals of course is associated with a certain randomness. Since it is not yet possible to "visualize" ahead the distribution which is to be examined, it is necessary to set a priori the separation threshold according to as good as possible guesses or approximations concerning the distribution, and thus, to realize a discriminator which only permits further processing signal values above or below the separation threshold. Yet, if there were available a greater amount of knowledge about the signals arriving during the next time section, then it should be better possible to make more precise observations. Thus, it is more advantageous to make instead of an a priori decision, an a posteriori decision in that, there are stored in a memory the signal quantities needed for an analysis and also all additional incoming signals and, after ordering the same in a distribution, there is carried out the separation of the thus involved signal classes. In this way there can be set with greater security a separation threshold, since, in the meantime, disturbing uncertainties have been eliminated.

The first step is data acquisition. The electrical signals or pulses delivered by a feeler or sensor element, with analogue detection, are infed for instance to a chain of amplitude discriminators. The signal is accepted according to its magnitude by one of the discriminators and stored in a subsequently connected integrator. The totality of the integrators arranged in circuit after the discriminators contains the distribution in the form of a histogram. With digital detection the electrical signals delivered by the feeler or sensor element are digitalized and stored as a value quantity in a storage or memory. This memory contains, after a corresponding rearrangement of the distribution, its portrayal as a histogram. The stored signal values appear in the form of individual signals or summation signals discretely in the channels. These channels are either individual integrators or vectors deposited in a digital storage. Also a particle analysis by mechanical filtering in sieve or filter stacks produces a histrogram in a manner such that, the sieve mesh functions as a discriminator and the sieve or filter itself constitutes a channel. The distribution throughout the entire sieve stack corresponds to a histrogram in that the values appear as summation weight of the particles contained in the individual sieves.

In a second step there is selected within the generated histogram a range which is to be examined, for instance a functionally coherent or consecutive number N of integrators, vectors or sieves. The stored values of this number of selected channels are individually compared with one another in order to find one channel whose stored value is smaller than each value in the other therewith compared channels. Thus there is determined as a first approximation a minimum in such selected range. Depending upon the selection of the means, for instance with digital evaluation of the signal quantity and with additional high resolution of the distribution spectrum, i.e. very narrow or a great many channels, there is recommended smoothing of the histogram, something which can be easily accomplished by the computer used in this case anyway.

The third step of the process entails checking the found minimum and thereafter reaching a decision. There exists for instance the possibility that the selected range encloses a flank of the distribution spectrum, in other words the sought-for minimum of the distribution is located outside of this range. In this case the determined minimum only indicates the lowest value of such section at the flank. The minimum which is to be found is located either between channels, whose stored values essentially increase from channel to channel or at least remain constant. Statistical scatterings at the neighborhood of the sought channel are taken into account in that the neighborhood is increased by further channels. Now if a coherent or consecutive number of channels, arranged directly to one side of the determined channel, show decreasing values, and a coherent or consecutive number of channels arranged at the other side show increasing values, then the second method step must be repeated with newly selected N-channels. This means nothing more than shifting the range to be examined within the histogram. With systematic shifting, the minimum, which indicates two classes of the distribution, appears in the range in which the values of the channels are individually compared with one another.

In a further step it is possible to retain or store the finally determined channel, whose stored signal value indicates the "correct" minimum, by means of a characteristic value which is correlated therewith. It is therefore now possible to evaluate both classes of such examined bimodal distribution.

In the case of a particle analysis for leukocytes the one class contains the erythrocyte fragments as artifacts and the other class contains the leukocytes. The values in the channels, belonging to the class of the leukocytes, now can be further evaluated, those belonging to the artifacts can be eliminated.

There will now be described hereinafter two embodiments for performance of the method. The one embodiment shows procedures carried out with the aid of digital means, for instance a microprocessor or a multipurpose computer, the other embodiment is performed with analogue means or a coaction of digital control with analogue networks. A commercially available microprocessor which can be advantageously employed is the Intel Model 8085A, of Intel Corporation.

In FIG. 1 there is indicated in a grouped together illustration an example of individual method steps which can be performed with the aid of discrete structured digital circuits and/or programable networks. The description to follow details the individual method steps.

1. Organization of the Memory:
   (i) guessing the size range of the expected particle distribution.
   (ii) defining the discrete step size.
   (iii) defining the number of K-channels which are to be used wherein:

$$K = \frac{\text{particle distribution}}{\text{discrete step size}}$$

(iv) allocation of an absolute particle size to each storage channel (discrimination according to particle volume; can be advantageously carried out in ascending sequence).
   (v) defining the decision criteria (for instance relative minima, incrementization and even others).
2. Signal Storage:
   (i) real time determination
   (ii) digitizing the signals delivered by the feeler or sensor element.
   (iii) Allocation of the digital values to the corresponding indexed storage channels. In other words the stored signal quantities available for analysis are ordered into a histogram within storages organized in K-channels.
   (iv) it is advantageous to select the storage channel addresses such that the digitalized particle signals constitute the storage channel addresses.
3. Preparation of the Signal Quantities:
   (i) each digitalization, here two dimensional, is afflicted with quantitization errors.
   (ii) it is advantageous to use a procedure, for instance by calling a sub-program, which reduces such quantization errors. It is possible for instance that the histogram is smoothed between the preceding step 2(iii) above described and the previously described comparison step where there is determined the smallest signal value.
   (iii) there can be employed a compensation of the first order (smoothing).
   (iv) if necessary there can be used a compensation of a higher order.
4. Selection of a Range in the Histogram:
   (i) to find the minimum there are set boundaries by the number N of coherent or consecutive storage channel addresses.
   (ii) the same procedure as just mentioned above is analogously carried out in order to find a possible maximum.
5. Finding the Minima:
   (i) the minimum is determined by mutual comparison of the signal values in the N-channels, while taking into account the criteria of rubric 4. above and according to the comparison step where there is determined in the N-channels the smallest signal value of the process as described heretofore.

6. Checking and Decision:
   (i) checking the determined minimum whether it is relative or absolute, according to the described comparison step between the signal value of the determined channel and the multiplicity of $P_L$-channels and $P_R$-channels, respectively.
   (ii) using the decision criteria upon the occurrence of relative minima according to rubric 1. above and according to the described step of the method where there is possibly repeated the described comparison step with a different selection of N-channels until there is determined the smallest signal value of the determined channel.
   (iii) the same is analogously carried out for a possible finding of the maximum.
   (iv) if there is not found any minimum (for instance idle measurement, no evaluatable separation of the classes), then the histogram is checked for analytical relevancy, for instance as to its haematological statement value or for defects in the equipment.

7. Use of the Determined Minimum:
   (i) forming the integral (counting) at both sides of the minimum (separation threshold).
   (ii) result output.
   (iii) initialing a new measurement by means of control signals which are formed with the aid of the characteristic value of the determined channel.
   (iv) delivering control signals to connected equipment for automatic sample processing, for dilution change.
   (v) instructions to the user.

Figure 2:
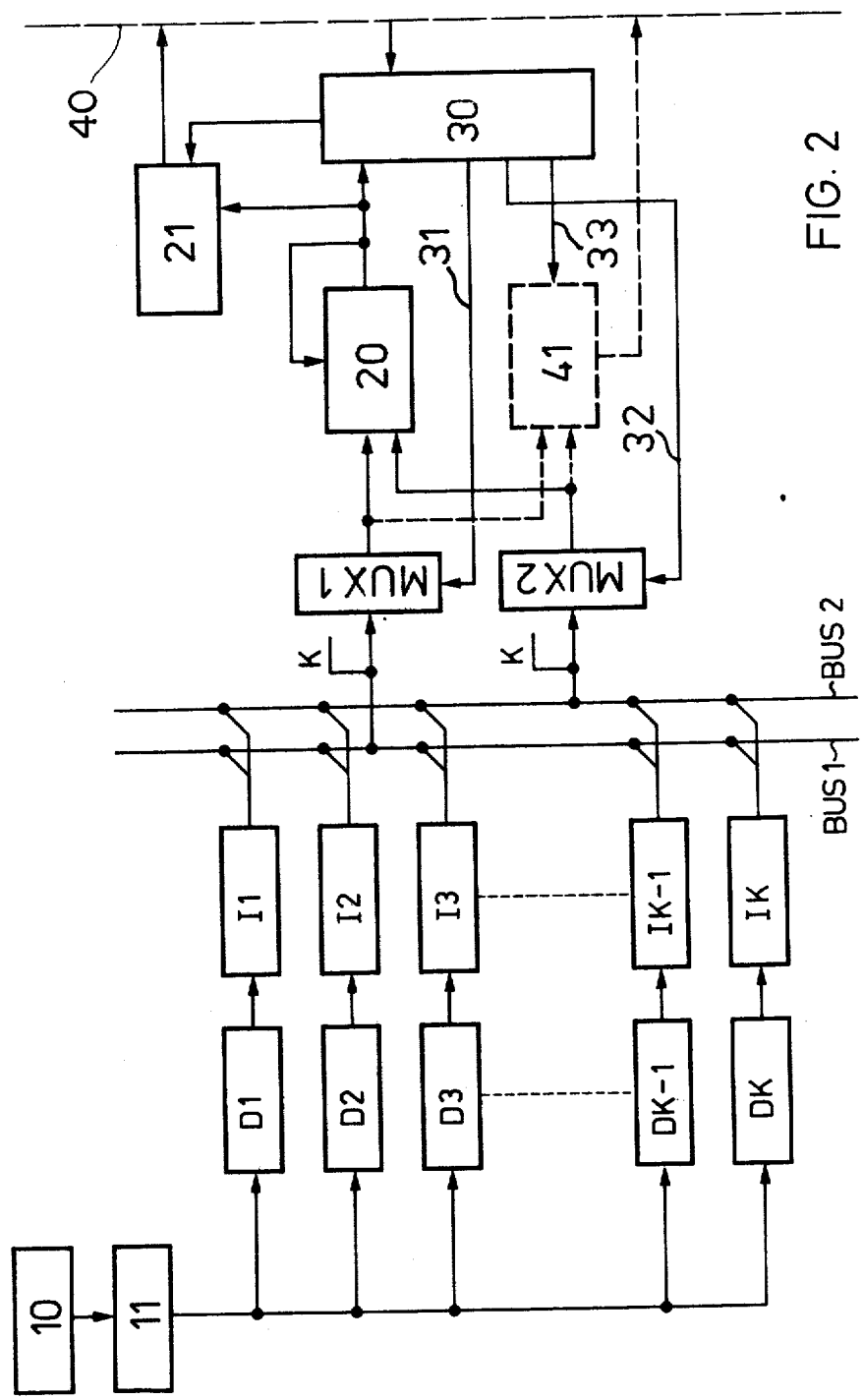
FIG. 2 shows an example of an analogue network for the described course of the method together with a control network for discrete or semi-integrated digital construction with fixed wired or exchangeable programs.

Turning attention now to FIG. 2 there will be recognized a system of K-discriminators D which, following fulfillment of the discriminating conditions, infeed the signals received from the feeler or sensor element 10 connected with amplifier 11 to integrators I. These K-integrators I form the memory or storage with K-channels. Two multiplexers MUX 1 and MUX 2, arranged in circuit after such memory, as well as an analogue comparator 20 controlled by such multiplexers, perform the comparison of the electrical values in the channels of a selected coherent number N. The selection of the channels is carried out by a control 30 which typically may be a logical network modified for the desired process. If there is provided for such control a microprocessor, such as Intel microprocessor 8085A, then there must be determined whether it would not be more advantageous to carry out a complete digital performance of the method. A signal from the analogue comparator 20 enables storing one or a number of channel characteristic values within the channel storages 21, wherein at least one is extinguished in each case as soon as there results from the comparison operation a still smaller signal value. An analogue storage 41 is provided for the storage of electrical values, such as individual signals or summation signals from an individual channel or signals which have been summed from a multiplicity of channel contents, for instance the integral of all signals or summation signals from channels at one side of the separation threshold. This storage belongs to the evaluation network and is therefore shown removed from the circuitry which performs the method.

Legends to FIG. 2:

10—Feeler or Sensor Element
11—Amplifier
$D_{Index}$—Discriminators
$I_{Index}$—Integrators
20—Analogue Comparator
21—Channel Characteristic Value Storage
30—Control Network
31—Signal Infeed For Channel Selection by MUX 1
32—Signal Infeed For Channel Selection by MUX 2
33—Signal Infeed to Storage Command in Analogue Storage
40—Interface to Evaluation Network
41—Analogue Storage While there are shown and described present preferred embodiments of the invention, it is to be distinctly understood that the invention is not limited thereto, but may be otherwise variously embodied and practised within the scope of the following claims. ACCORDINGLY,

What we claim is:

1. A method for determining a separation threshold for separating at least two signal classes in a signal quantity, composed of individual signals, which are converted by a feeler element into electrical signals and stored in a storage, comprising the steps of:
   (a) ordering the stored signal quantities which are present for analysis in storages organized into K-channels so as to form a histogram;
   (b) determining within a coherent number of N-channels of the histogram by mutual comparison of the signal values stored in the N-channels or values derived therefrom one of such channels whose signal value is smallest;
   (c) thereafter storing a characteristic value correlated to the thus determined channel as the separation threshold within the histogram so that there can be evaluated different signal values to different sides of such separation threshold;
   (d) comparing the signal value of the determined channel with each of the signal values of a multiplicity of $P_L$-channels directly following one side of the determined channel and with each of the signal values of a multiplicity of $P_R$-channels directly following the other side of the determined channel; and
   (e) if during step (d) above there prevails at least a signal value in subsequent $P_L$-channels or $P_R$-channels which is smaller than the signal value of the determined channel repeating step (b) above with a different selection of N-channels until the signal value of the determined channel is the smallest.

2. The method as defined in claim 1, further including the steps of:
   smoothing the histogram between the steps (a) and (b).

3. The method as defined in claim 1, further including the steps of:
   correlating for haematological use the range of the characteristic value of the K-channels to a particle volume range of 0–300 femtoliters.

4. The method as defined in claim 3, wherein:
   the channel characteristic values correspond to the particle values in femtoliter.

5. The method as defined in claim 4, wherein:
   $P_L$ is equal to $P_R$.

6. The method as defined in claim 4, wherein:
   $P_L$ is an integer and smaller than N/2.

7. The method as defined in claim 4, wherein:

$P_L$ is an integer and equal to N/2.

8. The method as defined in claim 1, wherein:
   the value of N corresponds to integer values between K/20 and K/5.

9. The method as defined in claim 1, wherein:
   $P_L$ is equal to $P_R$.

10. The method as defined in claim 1, further including the steps of:
    utilizing the signal value of the channel corresponding to the separation threshold as a quality criterion.

* * * * *